(12) United States Patent
Stokoe et al.

(10) Patent No.: US 11,927,580 B2
(45) Date of Patent: Mar. 12, 2024

(54) DETECTION OF BLOCKAGE IN A POROUS MEMBER

(71) Applicant: MSA TECHNOLOGY, LLC, Cranberry Township, PA (US)

(72) Inventors: Alexander Stokoe, Cambridge (GB); Harry Bullivant, Cambridge (GB); Shane Kelleher, Pittsburgh, PA (US)

(73) Assignee: MSA Technology, LLC, Cranberry Township, PA (US)

(*) Notice: Subject to any disclaimer, the term of this patent is extended or adjusted under 35 U.S.C. 154(b) by 431 days.

(21) Appl. No.: 17/204,361

(22) Filed: Mar. 17, 2021

(65) Prior Publication Data

US 2021/0199635 A1 Jul. 1, 2021

Related U.S. Application Data

(62) Division of application No. 16/199,019, filed on Nov. 23, 2018, now Pat. No. 10,983,103.

(51) Int. Cl.
*G01N 33/00* (2006.01)

(52) U.S. Cl.
CPC ..... *G01N 33/0062* (2013.01); *G01N 33/0006* (2013.01); *G01N 33/007* (2013.01)

(58) Field of Classification Search
CPC .......... G01N 33/0006; G01N 33/0062; G01N 33/007
See application file for complete search history.

(56) References Cited

U.S. PATENT DOCUMENTS

| | | | |
|---|---|---|---|
| 4,163,899 | A | 8/1979 | Burough |
| 5,753,797 | A | 5/1998 | Forster |
| 5,944,969 | A | 8/1999 | Scheffler |
| 7,034,943 | B1 | 4/2006 | Moeckli |
| 7,242,479 | B2 | 7/2007 | Moeckli |
| 7,318,335 | B2 | 1/2008 | Olesen |
| 7,413,645 | B2 | 8/2008 | Scheffler |
| 7,791,475 | B2 | 9/2010 | Clow |
| 7,886,576 | B2 | 2/2011 | Uber |
| 7,959,777 | B2 | 6/2011 | Scheffler |

(Continued)

FOREIGN PATENT DOCUMENTS

| | | |
|---|---|---|
| EP | 2104078 | 9/2009 |
| EP | 2189956 A2 | 5/2010 |

(Continued)

OTHER PUBLICATIONS

Vandersteen Audio Inc. "The Truth About Pistonic Driver Cones" web document (Year: 2018).*
Halfbakery "Acoustic Piston" web document (Year: 2018).*

*Primary Examiner* — John Fitzgerald
(74) *Attorney, Agent, or Firm* — BARTONY & ASSOCIATES LLC (57) ABSTRACT

A method of detecting at least a partial blockage in a porous member separating a first volume from a second volume or inner chamber of a device includes emitting pressure waves within the inner chamber by changing a volume of the inner chamber, measuring a response via a pressure sensor responsive to pressure waves positioned within the inner chamber, and determining if at least a partial blockage is present in the porous member based upon the response of the pressure sensor.

17 Claims, 5 Drawing Sheets

(56) References Cited

U.S. PATENT DOCUMENTS

| | | | |
|---|---|---|---|
| 8,958,595 B2* | 2/2015 | Hwang | H04R 17/00 |
| | | | 381/396 |
| 9,528,957 B2 | 12/2016 | Scheffler | |
| 9,784,755 B2 | 10/2017 | Scheffler | |
| 10,788,457 B2 | 9/2020 | Miller | |
| 10,788,458 B2 | 9/2020 | Miler | |
| 11,415,562 B2* | 8/2022 | Sexton | G01N 29/024 |
| 11,589,169 B2* | 2/2023 | Niekiel | H04R 9/00 |
| 2006/0157408 A1 | 7/2006 | Kuroda | |
| 2008/0252891 A1* | 10/2008 | Uber | G01N 21/1702 |
| | | | 73/24.02 |
| 2009/0267755 A1 | 10/2009 | Ropke | |
| 2013/0047703 A1 | 2/2013 | Stengel | |
| 2013/0186776 A1 | 7/2013 | Scheffler | |
| 2013/0186777 A1 | 7/2013 | Scheffler | |
| 2013/0192332 A1 | 8/2013 | Scheffler | |
| 2013/0193004 A1 | 8/2013 | Scheffler | |
| 2014/0273263 A1 | 9/2014 | Zanella, Sr. | |
| 2016/0206981 A1 | 7/2016 | Pursifull | |
| 2016/0320361 A1 | 11/2016 | Johansen | |
| 2017/0219515 A1 | 8/2017 | Davis | |
| 2017/0227498 A1 | 8/2017 | Miller | |
| 2017/0227499 A1 | 8/2017 | Miller | |
| 2018/0058280 A1 | 3/2018 | Pursifull | |
| 2019/0234841 A1 | 8/2019 | Spencer | |

FOREIGN PATENT DOCUMENTS

| | | |
|---|---|---|
| JP | 02128298 | 5/1990 |
| WO | WO2017136559 | 8/2017 |
| WO | WO20200106491 | 5/2020 |

* cited by examiner

PRIOR ART

DETECTION OF BLOCKAGE IN A POROUS MEMBER

CROSS-REFERENCE TO RELATED APPLICATIONS

This application is a divisional of U.S. patent application Ser. No. 16/199,019, filed Nov. 23, 2018, the disclosure of which is incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Many gas sensors include gas porous members/barriers or diffusion barriers that separate or partition the analytical components of the sensor from the environment the sensor is intended to monitor. Such porous members are commonly used to reduce or eliminate ingress of contaminants that may impede the operation of the sensor's analytical components and/or to isolate the analytical components as a source of ignition in the environment to which the sensor is exposed. When such porous members are used, the analyte gas(es) to be detected/monitored by the sensor must pass through the porous member to reach the analytical components of the sensor. The capability and effectiveness of analyte transport through the porous member directly impacts the speed, precision and accuracy with which the sensor can respond to changes in the relative concentration of the analyte in the external, ambient environment being monitored. Porous members are thus designed and/or selected such that the analyte transport through the porous member, in concert with the analytical components of the sensor, enable the sensor to respond to levels and/or changes in the relative levels of the analyte in the monitored environment at the nominal or minimal rate, precision and accuracy defined by the sensing application. Once a sensor is deployed, extraneous contaminants (arising in the normal operating environment or resulting from atypical events or maintenance activities) contacting or penetrating the porous member can either directly, or as a consequence of reaction with the porous member, inhibit analyte transport between the environment and the analytical components of the sensor. Such an inhibition in analyte transport through the porous member, resulting in deviation from the target sensor response rate to the analyte and/or deviation in precision/accuracy in assessment of absolute or relative changes in analyte concentration, is designated by the term "blockage" or "blocking". Additionally, the contaminant or condition causing the blocking is commonly referred to as the "blockage". A common example of blockage occurs in industrial environments where sensor response to the analyte can become partially or completely inhibited by overpainting, water, dirt/mud, insect or animal deposits, or by other extraneous diffusion-impeding substances. Failure to identify impairment of transport through the sensor porous member can result in under-detection or non-detection of analyte concentration levels exceeding safe environmental limits.

In addition to blockage of a diffusion or other sensor porous member, performance of the sensor itself may degrade over time. Prudence thus dictates that gas detection instrumentation be tested regularly for functionality. It is a common practice to, for example, perform a "bump check," or functionality check on portable gas detection instrumentation on a daily basis. The purpose of this test is to ensure the functionality of the entire gas detection system, commonly referred to as an instrument. A periodic bump check or functionality check may also be performed on a permanent gas detection instrument to, for example, extend the period between full calibrations. Gas detection systems include at least one gas sensor, electronic circuitry and a power supply to drive the sensor, interpret its response and display its response to the user. The systems further include a housing to enclose and protect such components. A bump check typically includes: a) applying a gas of interest (usually a gas including a known concentration of the target gas or the analyte gas which the instrument is intended to detect (or a simulant therefor), which may be a zero or other concentration); b) collecting and interpreting the sensor response; and c) indicating to the end user the functional state of the system (that is, whether or not the instrument is properly functioning).

As described above, such bump tests are performed regularly and, typically, daily for portable gas detection instruments. Bump checks provide a relatively high degree of assurance to the user that the gas detection device is working properly. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any gas porous protection and/or diffusion member or membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is interpreted properly. Moreover, the bump check ensures that the indicator(s) or user interface(s) (for example, a display and/or an annunciation functionality) of the gas detection instrument is/are functioning as intended.

However, a periodic/daily bump check requirement has a number of significant drawbacks. For example, such bump checks are time consuming, especially in facilities that include many gas detection systems or instruments. The bump check also requires the use of expensive and potentially hazardous calibration gases (that is, a gas having a known concentration of the analyte gas or a simulant therefor to which the sensor is responsive). Further, the bump check also requires a specialized gas delivery system, usually including a pressurized gas bottle, a pressure reducing regulator, and tubing and adapters to correctly supply the calibration gas to the instrument. The requirement of a specialized gas delivery system often means that the opportunity to bump check a personal gas detection device is limited in place and time by the availability of the gas delivery equipment. Moreover bump checks and other calibrations with test gas require someone that is trained on the device and in performing the test.

Recently, a number of systems and methods have been proposed to reduce the number of bump tests required. Such systems may, for example, include electronic interrogation of a sensor and/or a test of the transport path to the sensor, including through a diffusion or other barrier (without application of an analyte gas or a simulant therefor). Nonetheless, it remains desirable to develop improved testing systems and methodologies to, for example, reduce the number of bump checks required for sensors.

SUMMARY

In one aspect, a method of detecting at least a partial blockage in a porous member separating a first volume from a second volume or inner chamber of a device includes emitting one or more pressure waves within the inner chamber by displacing/changing a volume of the inner chamber, measuring a response via a pressure sensor responsive to the one or more pressure waves positioned within the inner chamber, and determining if at least a partial blockage is present in the porous member based upon the response of the pressure sensor. The first volume may, for example, be an ambient environment. In a number of embodiments, a gas sensor is positioned within the inner chamber.

In that regard, in a number of embodiments, a method of detecting at least a partial blockage in a porous member separating an inner chamber of a device, in which at least one gas sensor responsive to target gas is positioned, and an ambient environment includes emitting one or more pressure waves within the inner chamber by displacing/changing a volume of the inner chamber, measuring a response via a pressure sensor responsive to the one or more pressure waves positioned within the inner chamber, and determining if at least a partial blockage is present in the porous member based upon the response of the pressure sensor.

The volume of the inner chamber may, for example, be changed by movement/displacement of a moveable element in fluid connection with the inner chamber. In a number of embodiments, the moveable element includes a piston. In a number of embodiments, the moveable element includes a diaphragm.

The method may further include moving/displacing the moveable element via a drive system in operative connection with the moveable element. In a number of embodiments, the drive system includes a motor in operative connection with the moveable element. The method may, for example, further include controlling the drive system to oscillate the motion of the moveable element. This, may for example, occur during in an interrogation mode of the device in the case that the device is a sensor device. In a number of embodiments, the drive system is controlled to oscillate the moveable element in a generally sinusoidal manner. The frequency of oscillation may, for example, be in the range of 1 Hz to 200 Hz in a number of embodiments. In a number of embodiments, the frequency of oscillation is less than 10 Hz. The oscillation may, for example, occur at a single frequency.

In a number of embodiments, a measured amplitude in the response of the pressure sensor is used in determining if at least a partial blockage is present in the porous member. The value of any frequency of oscillation (in embodiments in which the moveable element is oscillated) may not, for example, be essential in determining if at least a partial blockage is present in the porous member. However, a measured response frequency may, for example, be analyzed to indicate whether or not there is a problem or malfunction in a device or system hereof (for example, such malfunctions include leaks, motor malfunction, moveable element fatigue, etc.)

In a number of embodiments, the moveable element is moved/displaced to create a predetermined volume displacement of the inner chamber to emit the one or more pressure waves. In a number of embodiments, the moveable element is moved/displaced to create a volume displacement of at least 1% or at least 1.5% of the volume (that is, the total volume) of the inner chamber to emit the one or more pressure waves.

In a number of embodiments, the porous member is a porous frit. In a number of other embodiments, the porous member is a hydrophobic, oleophobic or multiphobic porous member of membrane. See, for example, U.S. Pat. No. 5,944,969, the disclosure of which is incorporated herein by reference. The porous member may, for example, be hydrophobic. As used herein, the term "hydrophobic" refers generally to a porous member through which aqueous liquids are substantially immobile (that is, a hydrophobic porous member is resistant or substantially resistant to the bulk flow of water therethrough at internal pressures generally experienced in use of the devices or systems hereof). As used herein, the term "oleophobic" refers generally to a porous member through which non-aqueous liquids are substantially immobile (that is, an oleophobic porous member is resistant or substantially resistant to bulk flow of low-surface tension liquids therethrough at internal pressures generally experienced in devices and systems hereof). As used herein, the phrase "low-surface tension liquids" refers generally to liquids having a surface tension less than that of water. Diffusion barriers that are both hydrophobic and oleophobic are referred to as "multiphobic". The diffusion barriers of the present invention may also substantially chemically inert and thermally inert under the conditions in which the devices and system hereof are used. An analyte or target species is mobile through the porous members of membranes in its gas phase in gas detection devices, systems and/or methods hereof.

In a number of embodiments, a plurality of gas sensors is positioned within the inner chamber. Such gas sensors may, for example, include one or more electrochemical gas sensors, one or more combustible gas sensor, one or more infrared sensors, one or more photoacoustic sensors and/or other types of gas sensors.

In another aspect, a device includes a housing including an inner chamber and a port, a porous member in operative connection with the port to separate the inner chamber from an outer volume (for example, the ambient environment), a source of pressure change in fluid connection with the inner chamber, the source of pressure change including a moveable element which is movable to change/displace a volume within the inner chamber; a pressure sensor responsive to pressure change within the inner chamber; and circuitry in operative connection with the pressure sensor to determine if at least a partial blockage is present in the porous member based upon a response of the pressure sensor. In a number of embodiments, a gas sensor is positioned within the inner chamber.

In that regard, in a number of embodiments, a gas sensor device to detect an analyte gas in an ambient environment includes a housing including an inner chamber and a port, a porous member in operative connection with the port to separate the inner chamber from the ambient environment, at least one sensor responsive to a target gas positioned within the inner chamber, a source of pressure change in fluid connection with the inner chamber, the source of pressure change including a moveable element which is movable to change/displace a volume within the inner chamber, a pressure sensor responsive to pressure change within the inner chamber; and circuitry (for example, control circuitry) in operative connection with the pressure sensor to determine if at least a partial blockage is present in the porous member based upon a response of the pressure sensor.

In a number of embodiments, the volume of the inner chamber is changed/displaced by displacement of a moveable element in fluid connection with the inner chamber. The moveable element may, for example, include a piston or a diaphragm. In a number of embodiments, the moveable element includes a diaphragm. The gas sensor or other device hereof may further include a drive system in operative connection with the moveable element. The drive system may, for example, be operable to oscillate the motion of the moveable element. This may, for example, occur in an interrogation mode of a gas sensor device as described above. In a number of embodiments, the drive system is adapted or configured to be controlled to oscillate the moveable element in a generally sinusoidal manner. The frequency of oscillation may, for example, be in the range of 1 Hz to 200 Hz in a number of embodiments. In a number of embodiments, the frequency of oscillation is less than 10 Hz. The oscillation may, for example, occur at a single frequency.

As also described above, in a number of embodiments, the porous member is a porous frit or a hydrophobic membrane. In a number of embodiments, a plurality of gas sensors is positioned within the inner chamber.

In a number of embodiments, the circuitry (in methods, devices and/or systems hereof) is also in operative connection with the moveable element to move the moveable element to create a predetermined volume displacement of the inner chamber to emit one or more pressure waves. In a number of embodiments, the moveable element is moved to create a volume displacement of at least 1% or at least 1.5% of the volume (that is, the total volume) of the inner chamber to emit the one or more pressure waves.

In a further aspect, a method of detecting at least a partial blockage in a porous member separating an inner chamber of a device from an ambient environment, wherein at least one gas sensor responsive to target gas is positioned within the inner chamber and the device further includes a sampling pump to pump air from the ambient environment into the inner chamber, includes controlling the sampling pump to vary pressure, measuring a response via a pressure sensor positioned within the inner chamber, and determining if at least a partial blockage is present in the porous member based upon a response of the pressure sensor. In a number of embodiments, the sampling pump is positioned within the inner chamber and draws gas from the ambient environment into the inner chamber.

The present devices, systems, and methods, along with the attributes and attendant advantages thereof, will best be appreciated and understood in view of the following detailed description taken in conjunction with the accompanying drawings.

DETAILED DESCRIPTION

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of various embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Representative embodiments of devices, systems and methods hereof are described in connection with detection of blockage in a porous member separating an inner chamber including one or more sensors from an outer or ambient environment. However, one skilled in the art appreciates that the devices, system and method hereof may be used in connection with the detection of blockage in any porous member used to separate one volume from another.

As used herein and in the appended claims, the singular forms "a," "an", and "the" include plural references unless the context clearly dictates otherwise. Thus, for example, reference to "a sensor" or "a porous member" includes a plurality of such sensors or porous members and equivalents thereof known to those skilled in the art, and so forth, and reference to "the sensor" or "the porous member" is a reference to one or more such sensors or porous members and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

As used herein, the term "circuit" or "circuitry" includes. but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software.

The term "control system" or "controller," as used herein includes, but is not limited to, any circuit or device that coordinates and controls the operation of one or more input or output devices. For example, a controller can include a device having one or more processors, microprocessors, or central processing units (CPUs) capable of being programmed to perform input or output functions.

The term "processor," as used herein includes, but is not limited to, one or more processor systems or stand-alone processors, such as microprocessors, microcontrollers, central processing units (CPUs), and digital signal processors (DSPs), in any combination. A processor may be associated with various other circuits that support operation of the processor, such as a memory system (for example, random access memory (RAM), read-only memory (ROM), programmable read-only memory (PROM), erasable programmable read only memory (EPROM)), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

In a number of studies hereof, devices or instruments hereof include one or more combustible gas sensors and/or electrochemical gas sensors. Although combustible gas sensors and electrochemical gas sensors were studied, the devices, systems and methods may be used in connection with any sensor (for example, infrared sensors, photoacoustic sensors, etc.) or any other device in which a porous member or membrane separates an inner chamber or volume from an outside environment. Catalytic combustible gas sensor devices, electronic interrogation thereof and resulting corrections are, for example, described in U.S. Patent Application Publication No. 2014/0273263 and U.S. patent application Ser. No. 15/597,933 and Ser. No. 15/597,859, the disclosures of which are incorporated herein by reference. Electrochemical gas sensors, electronic interrogation techniques and resulting corrections are, for example, disclosed in U.S. Pat. Nos. 7,413,645, 7,959,777, 9,784,755, and 9,528,957, and in U.S. Patent Application Publication Nos. 2013/0186777 and 2017/0219515, the disclosures of which are incorporated herein by reference.

Using electronic interrogation systems, devices and methods, one has the ability to electronically interrogate a sensor, determine changes in sensor performance thereby, and compensate sensor output so that the sensor response is acceptable, thereby extending the period of time between (or eliminating) bump checks. Electronic interrogation of a sensor may, for example, include applying electrical energy to an electrode or sensor element and measuring a response to the application of electrical energy and/or an electrical property of the electrode or sensor element to determine a state of the sensor. Electronically interrogating a sensor, however, cannot account for or detect blockage of the porous member that separates/protects the sensor from the ambient environment or outside world. Combining electronic interrogation of the sensor with systems, devices and methods of detecting blockage of such a porous member, provides the ability to further reduce or eliminate bump testing of the instrument.

As a metric, blockage may directly designate impedance of analyte transport through the porous member and/or designate the resultant changes in sensor performance resulting from this transport impedance. Blockage may, for example, be metered in a continuous measure. For example, blockage may be metered as a percentage, ranging from 0% when analyte transport through the porous member is normal or nominal to 100% marking total inhibition of analyte transport between the sensor analytical components and the monitored environment. Blockage may also be metered as discrete states with designations such as unblocked (indicating typical or normal analyte transport through the porous member) or partial (indicating impedance of analyte transport beyond typical or normal but less than complete transport inhibition) or complete (indicating total inhibition of analyte transport through the porous member). Alternatively, blockage can be ascribed to boolean states, with an unblocked state indicating inhibition of analyte transport through the porous member falls below a designated acceptable limit, and a blocked state indicating analyte transport inhibition exceeds the designated limit. Adequate measurement in detecting and designating blockage (and/or resultant impairment to sensor performance) is important for assurance of sensor function. As described above, failure to identify impairment of transport through the sensor porous member can result in under-detection or non-detection of analyte concentration levels exceeding safe environmental limits.

U.S. Patent Application Publication Nos. 2017/0227498 and 2017/0227499, assigned to the assignee hereof, the disclosures of which are incorporated herein by reference, describe devices, systems and methods used to detect flow through a porous member, membrane or barrier (for example, a diffusion barrier) of, for example, a sensor for detecting a target or an analyte gas. Such porous members may, for example, be porous metal frits or porous polymeric membranes in a number of representative embodiments. In the devices, systems and methods thereof, a source, generator or transmitter of acoustic/pressure waves such as a speaker is played into a volume or chamber behind (that is, on the sensor side and opposite the ambient side) of a porous member such as a porous frit or a porous membrane. A response to the generated acoustic/pressure waves (for example, sound) is measured by a pressure/acoustic wave sensor sensor or receiver such as a microphone and is related to gas transport through the membrane.

Such devices, systems and methods may, for example, be used in fixed or portable gas instruments. In the case of a fixed (as opposed to portable) gas instrument, the instrument is calibrated when it is put into service. As described above, after placement in service, it is recommended to frequently "bump test" the instrument to check for gas flow to the sensor and that the sensor responds as expected. As also described above, to bump test an instrument, the user applies a target/analyte gas (or a simulant gas to which the sensor is responsive) of a known concentration to the instrument and checks the instrument for an expected or acceptable response. If the sensor response is acceptable (using, for example, predetermined thresholds), the user can then calibrate the instrument to the known concentration of the target gas.

In U.S. Patent Application Publication Nos. 2017/0227498 and 2017/0227499, an acoustic wave or waves was transmitted from a source/speaker within a sensing chamber to interact with the porous member and with any blockage thereof to detect a blockage of a porous member separating a gas sensor within the sensing chamber from the ambient environment (in which the concentration of the analyte gas it to be determined). Signals were then received by an acoustic sensor/microphone. Such microphones convert sound (which propagates as an audible wave of pressure) into an electrical signal (typically in the units of decibels). The response was processed and correlated to a loss in flow through the porous member and/or, in the case of a sensor, a loss in gas response of the sensor. There are a number of ways to analyze and/or to process the data to determine the presence and/or degree of a blockage. In general, a correlation was made between measured sound and blockage of the porous member. The pressure changes created by a speaker suitable for use in a gas sensor is typically in the range of 0 to 5 Pascal or Pa.

Figure 1:
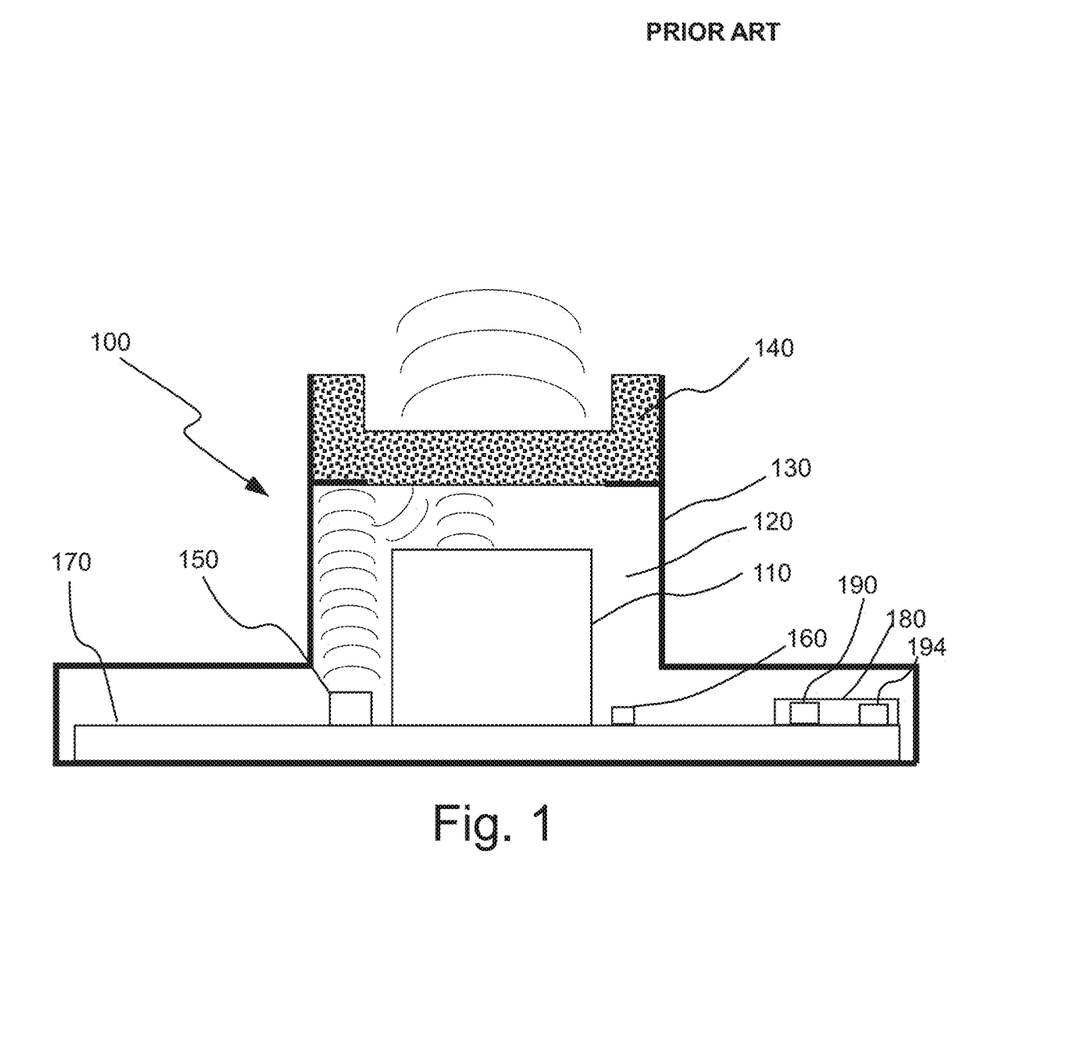
FIG. 1 illustrates an embodiment of a gas sensor device or instrument in which an acoustic wave is generated by a speaker within a chamber or volume of a sensor device and a microphone within the chamber of volume measures a response.

In device 100 of FIG. 1, for example, a speaker 150 and a microphone 160 are also positioned within an inner chamber 120. It is not necessary to acoustically isolate speaker 150 and microphone 160 from the remainder of inner chamber 120 and sensor 110 or to narrowly channel the propagation of acoustic/pressure waves therebetween. In the illustrated embodiment, sensor 110, speaker 150 and microphone 160 are in electrical connection with circuitry including a printed circuit board 170 which may be in electrical connection with control circuitry, control system or controller 180 illustrated schematically in FIG. 1, which may be positioned within and/or outside of explosion proof housing 130. Control circuitry 180 may for example, include a processor system 190 (including one or more processors such as microprocessors) and a memory system 194 (including one or more memory modules such as memory drives) in operative connection with processor system 190. Memory system 194 may, for example, include one or more algorithms stored therein and executable by processor system 190.

As illustrated in FIG. 1, acoustic waves propagate within chamber 120 toward porous member or frit 140. Without limitation to any mechanism, some of the acoustic waves pass into frit 140, and some of the sound waves are reflected back into inner chamber 120. In that regard, of the acoustic waves that pass into frit 140, some are absorbed in frit 140, some are reflected back into inner chamber 120 (from which the acoustic waves emanated), and some pass through frit 140 into the ambient environment outside of explosion proof housing 130. The acoustic waves that are passed through frit 140 and outside of explosion-proof housing 130 are "lost" acoustic waves, which are very relevant to the degree of blockage of frit 140. When frit 140 is blocked, less acoustic waves (for example, sound waves) are lost, and more acoustic waves are reflected back into chamber 120.

In a number of studies of the devices systems and methods of U.S. Patent Application Publication Nos. 2017/0227498 and 2017/0227499, multiple frequencies were generated by speaker 150. If, for example, one examined what sound is received by microphone 160 in the frequency domain, one should be able to readily pick out the frequencies that were generated. One could then set a threshold at each frequency for a magnitude and/or phase for what a blocked or unblocked response should be. Analysis may also be made in the time domain (wherein thresholds may, for example, be set for a magnitude and/or time delay of a response). In the time domain, a driving force including multiple frequencies may, for example, be generated by the speaker. It was discovered that at some frequencies the response was actually quieter/decreased when frit 140 was blocked. It was also found that the resonances of chamber 120 may be significant, and in the same frequency region as the interrogation signal. Furthermore, it was discovered that information regarding blockage of the porous member could be discerned from measured changes in amplitude and/or changes in phase.

Although a speaker/microphone combination is a very good retroreflective system for detecting and even characterizing blockages in porous members, addition of a speaker/microphone combination to many systems results in a significant increase in manufacturing complexity and/or cost. In a number of systems hereof, pressure changes such as relatively low frequency or individual pulse pressure waves are created by movement (for example, mechanical oscillation) of a moveable member or element within a volume or inner chamber to, for example, change/displace the volume within the chamber, thereby creating the pressure changes measurable by a pressure sensor (that is, a device for measuring pressure and providing an output in force per unit area such as pounds per square inch) other than a microphone within the chamber. As used herein, the term "inner chamber" refers to all volume of the device or system in fluid connection on the side of a porous member opposite the ambient environment side of the porous member. In other words, the porous member separates the ambient environment or atmosphere from the inner chamber. The inner chamber may, for example, be divided into two or more sections or compartments which are in fluid connection with each other. In a number of studied embodiments hereof, for example, illustrated in FIG. 2A, a combustible gas sensor device or instrument 100a was tested which included a sensor 110a within an inner chamber 120a created by a housing 130a, which may, for example, be an explosion-proof housing in the case device 100a is to be used in connection with an environment which may include combustible or flammable gases. However, an explosion-proof housing is not always necessary. For example, portable devices typically do not include explosion-proof housings. In a number of embodiments hereof, the devices or systems hereof are portable (that is, readily carried or moved). In a number of embodiments, such portable devices or system are handheld devices or systems. A porous member 140a was placed in connection with inlet port 134a between the outside environment to be tested and inner chamber 120a. Sensor 110a may, for example, be a catalytic combustible gas sensor as described above.

Figure 2A:
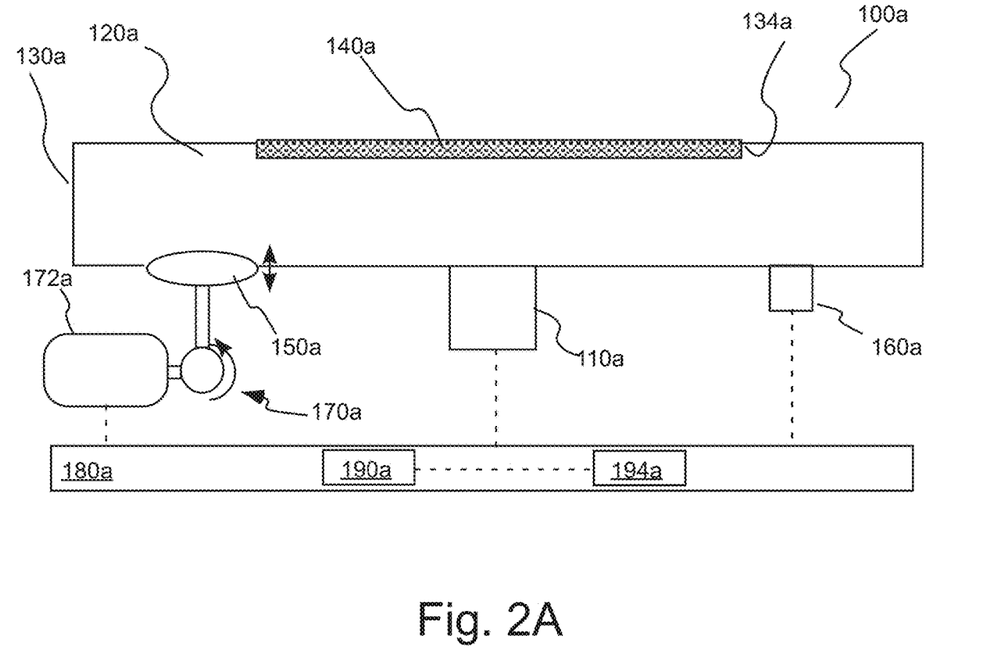
FIG. 2A illustrates an embodiment of a gas sensor device or instrument hereof in which one or more pressure waves (for example, oscillating pressure waves) are mechanically created within a chamber of volume of a sensor device and a pressure sensor within an inner chamber of the device measures a response.

In the embodiment of device 100a, a moveable element such as a diaphragm 150a and a pressure sensor 160a are also positioned within chamber 120a. Other moveable elements such as one or more pistons or plungers (which may, for example be sealed to chamber 120a) may also be used. In a number of studies, in an interrogation mode of the device, one or more pressure waves or pressure oscillations were generated within chamber or volume 120a via movement of a moveable element such as diaphragm 150a which is operatively connected to a drive system 170a including, for example, a motor 172a to move/oscillate diaphragm 160a. The movement of the moveable element may, for example, result in a known volume displacement (which may stay constant or vary over time in the case of repeated movement). The combination of the drive system and the moveable element may be referred to as a "positive displacement drive." Actuators other than rotary motors may also be used herein (for example, electromagnetic solenoid actuators, pneumatic actuators, hydraulic actuators, manual actuators, spring-based actuators etc.). The pressure changes/oscillations were measured within chamber or volume 120a via pressure sensor or transducer 160a. In that regard, movement of diaphragm 150a creates pressures changes within common chamber 120a, which are then measured by pressure sensor 160a.

In a number of embodiments, motor 172a may, for example, be a pump motor of a pump used to draw environmental or ambient gas into the volume 120a (sometimes referred to as a sampling pump). Alternatively, a dedicated motor may be used in drive system 170a. If motor 172a is also used to drawing environmental gas into volume 120a, any loss of power associated with, for example, parallel operation to drive the moveable element hereof should not significantly affect the use of motor 172a to draw environmental gas into volume 120a.

In a number of representative embodiments in which moveable element 150a is oscillated, the pressure sensor data was transformed into the frequency domain using a Fast Fourier Transform or FFT. In a number of embodiments, the frequency range of interest is subsequently examined to identify the driven oscillatory pressure signal as a peak in the spectrum. The sum of the frequency bins around this peak provides a pressure magnitude that may, for example, be used to determine porous membrane blockage. In general, a higher measured pressure magnitude corresponds to more blockage of the porous member 140a, because flow of the air through porous member 140a is restricted. Increasing blockage results in increasing sensor response times. In a number of embodiments, once the measured pressure magnitude reaches a predetermined threshold value, device or instrument 100a may alert the user that porous member 140a is blocked. Upon determination of blockage, porous member 140a may, for example, be replaced.

Although the moveable element may be oscillated in a number of embodiments, oscillation is not necessary. In a number of embodiments, for example, a single actuation whereby the volume 120b observes a step change in pressure, movement or "ping" of the moveable element may be effected and the response measured. In a number of embodiments, the moveable element may be actuated periodically without being continuously oscillated. In a number of embodiments in which moveable element 150a is oscillated, a frequency of oscillation may, for example, be in the range of 1 Hz to 200 Hz.

In general, the amplitude of the volume change/oscillation created by the moveable element hereof should be great enough to create a reasonably measured change in pressure of a chamber of volume such as volume 120a over expected environmental operating conditions when the porous member is deemed "unblocked". The term "reasonably measured" as used herein is defined to be an amplitude of at least four quantized pressure steps for a system with a digital pressure sensor or 4 ADC levels above the noise level for an analog pressure sensor.

In a number of embodiments, a drive scheme for the moveable element is a low frequency (that is, less than 10 Hz) sinusoid drive scheme in a completely sealed system. However, data analysis approaches such an FFT approach are robust to imperfect sinusoids and any oscillating signal with, for example, a 'significant' fundamental frequency can be used. As used in herein, a significant fundamental frequency refers to an oscillating signal having a THD (Total Harmonic Distortion) of under 40%. Studies of models and test data hereof have shown that the precision and the dynamic range of the occlusion detection method hereof are increased as the oscillation frequency is decreased. However the lower the frequency, the more susceptible the system is to disruption by leaks in the gas volume 120b. The drive frequency may be selected on a level of confidence of the seal of the system.

In a number of embodiment, a measured peak magnitude frequency may be analyzed to indicated whether or not there is a problem or malfunction in the system. For example, if motor is operating at a known frequency (for example, 20 Hz), and one measures a peak magnitude frequency that is significantly different than 20 Hz, this result indicates a problem or malfunction. For example, such problems or malfunctions may include leaks, motor malfunction, diaphragm fatigue, etc.

As described above, in a number of embodiments, a single ping of movement of the moveable element may be used observe blockage. For example, such a blockage may be observed by timing the pressure decay. The oscillation-FFT method described herein essentially carries out the same function but with oversampling measurement time*Frequency times and averaging.

In a number of embodiments, the pressure sensor or sensing element (such as pressure sensor 160a or other pressure sensors hereof) of devices, instruments and systems hereof are able to measure discrete pressure samples at a rate that incurs a measurement Nyquist frequency (that is, a frequency that is half of the sampling rate of the discrete signal processing system) significantly (that is, at least 10×) above the drive frequency range. The pressure sensor or pressure sensing element may, for example, include a discrete pressure sensor ASIC that measures barometric pressure and digitally communicates pressure samples to the CPU. An example of such a pressure sensor suitable for use herein is, such as the MS5607-02BA03 sensor available from TE Connectivity Measurement Specialties, having a regional headquarters in Berwyn, Pennsylvania. Alternatively, an analogue barometric or differential pressure sensor (for example an ABPLLNN600MGAA3 sensor, available from Honeywell of Morris, New Jersey), may, for example, be used in combination with analog-to-digital converter or ADC electronics to provide the pressure samples (for example, to calculate an FFT).

As compared to use of sound generation and measurement by a microphone, the low frequency, positive displacement, pressure sensing approach has the advantage of directly measuring the gas movement through the porous member, The approach hereof provides a detection method with the potential to be completely independent of occlusion material. Further, use of a single drive frequency allows quick measurements as it is not necessary to sweep a range of frequencies and compare to complex frequency responses for a range of material blockages.

In general, the moveable member hereof created a predetermined volumetric displacement within, for example, some assumed frequency range (that is, at whatever frequency or frequency range the drive system is set). After creation of the predetermined displacement, the pressure amplitude is measured and compared to an expected pressure amplitude so that the difference between the measured and expected pressure amplitude may be determined. From that difference, a determination may be made on the blockage status (for example, a degree of blockage) of the porous member. In acoustic methods, a sound of pressure wave of a known frequency is created via an uncontrolled amount of displacement (which will vary depending on the load or level of blockage). In other words, a known frequency and an unknown displacement are applied and the resulting phase shift and/or amplitude are measured to make a blockage determination. In many cases, the phase shift and amplitude are determined to make a blockage determination.

It has been determined that, in a number of embodiments hereof, a displacement of at least 1% or at least 1.5% of the volume of the inner chamber should be created by the moveable element hereof. In a number of embodiments, the pressure change resulting from the movement of the moveable element hereof is at least 1 kPa. In a number of embodiments, the pressure change is in the range of approximately 1-2 kPa.

As discussed in connection with speaker 150 above, it is not necessary to isolate diaphragm 150a and pressure sensor 160a and the pressure changes/waves propagated therebetween from the remainder of chamber 120a and sensor 110a or to narrowly channel the propagation of pressure oscillations/waves therebetween. In the illustrated embodiment, sensor 110a, diaphragm 150a and pressure sensor 160a are in electrical connection with circuitry/control circuitry 180a illustrated schematically in FIG. 2A, which may be positioned within and/or outside of housing 130a. Control circuitry 180a may for example, include a processor system 190a (including one or more processors such as microprocessors) and a memory system 194a in operative connection with processor system 190a. Memory system 194a (including one or more memory modules such as memory drives) may, for example, include one or more algorithms stored therein and executable by processor system 190a.

Figure 2B:
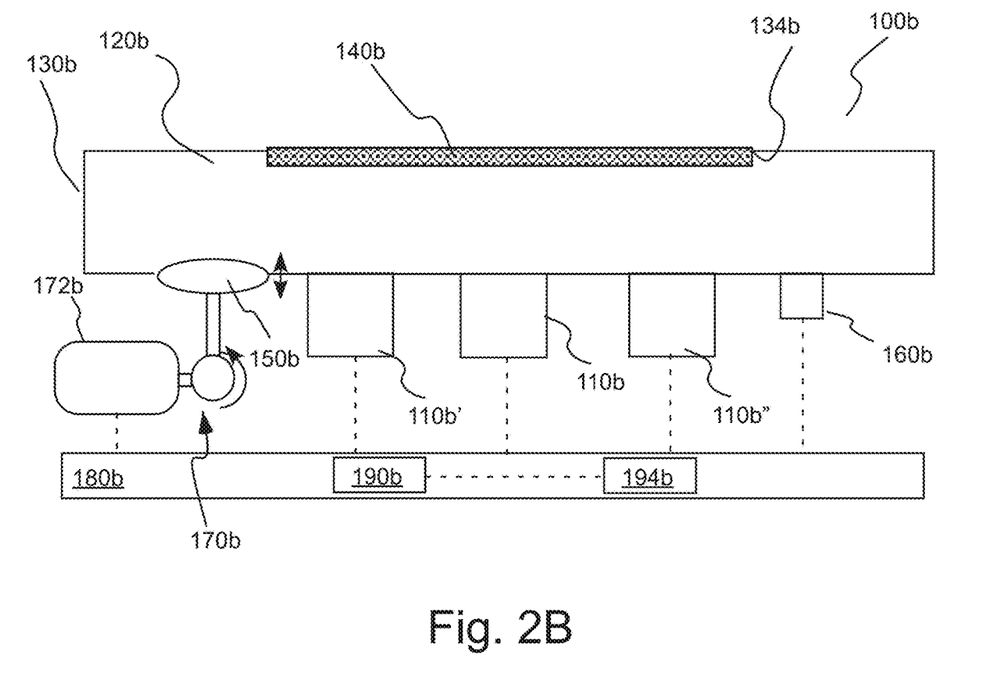
FIG. 2B illustrates another embodiment of a gas sensor device or instrument hereof similar in construction and operation to the device of FIG. 2A wherein multiple sensors of the same or different types are within the inner chamber.

FIG. 2B illustrates another embodiment of a device or instrument 100b which is very similar in operation and construction to device or instrument 100a. Elements of device 100b are numbered similarly to corresponding elements of device 100a, but the designation "b" is replaced with the designation "a". Unlike, device 100a, however, device 100b is designed so that multiple sensors (three sensors 110b, 110b' and 110b" in the illustrated embodiment) are in fluid connection within inner chamber 120b, which allows gas to pass through and keeps water and other debris from the atmosphere out. The three sensors share a common inlet port (via porous member or membrane 140b positioned within the inlet port or opening). The three sensors also share the same internal volume within the instrument, which is sealed everywhere such that the only path for air flow is through porous member or membrane 140b.

In a number of studied embodiments, a sensor instrument 100b was tested which included a combustible sensor 110b and two electrochemical sensors 110b' and 110b". Inner chamber 120b may, for example, be created by an explosion-proof housing 130b and a porous member in the form of a porous member 140b may be used (for example, a sintered metal frit which provides a barrier to prevent explosion or a polymeric, porous membrane). In a number of embodiments, the detection pressure wave associated with porous member blockage may be enhanced through design of the geometry of the chamber coupling the pressure wave generator/pressure sensor to the porous member. For example, reducing the size of the chamber or volume increases blockage response sensitivity.

Figure 3:
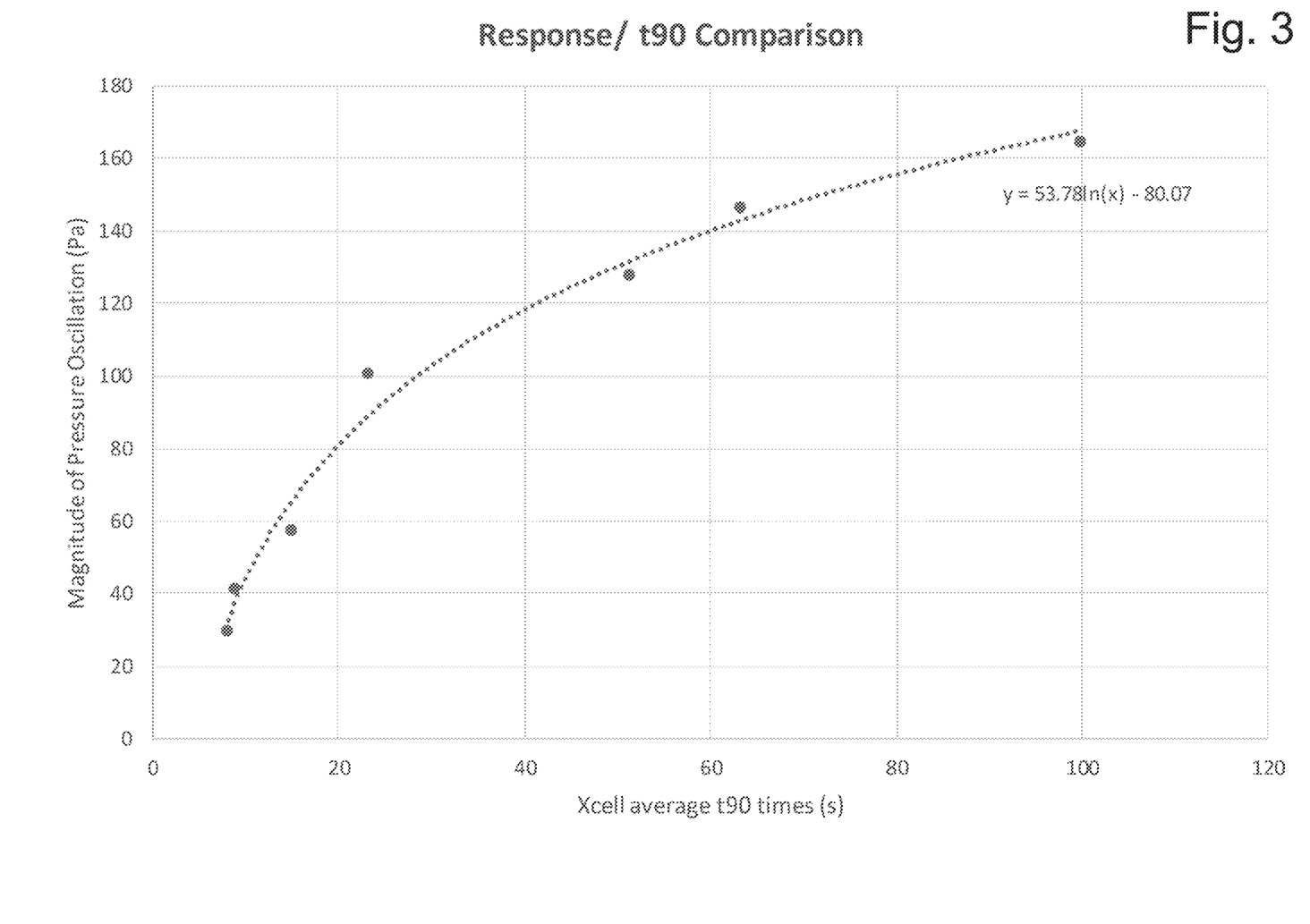
FIG. 3 illustrates response time ($t_{90}$) of a sensor as a function of measured magnitude or pressure oscillation (which increases with increasing blockage) as measured by the pressure sensor within an inner chamber of the device of FIG. 2B.

FIG. 3 illustrates response time ($t_{90}$) of a sensor as a function of measure magnitude of pressure oscillation (which increases with increasing blockage) as measured by the pressure sensor of the device of FIG. 2B. The $t_{90}$ response time is the time, in seconds, required for the sensor to reach 90% of the response. This measure of gas detector response time (referring to the aforementioned portable instrument) can be used as a method to determine the level of blockage preventing the analyte diffusing through the porous member to the sensors. The degree of blockage is increasing with sensor $t_{90}$ in FIG. 3. Blockage level may, for example, be defined as a time increase from an unblocked or "clean" filter detector $t_{90}$, to the $t_{90}$ response time of a detector once an occlusion material is present on the porous member. In the studies of FIG. 3, it was assumed that if the sensor had settled to within 90% of its response before 120 seconds, a percent blockage could be determined as described above. If, the sensor did not settle to within 90% of its response within 120 seconds, the porous member was determined to be completely blocked. In general, the magnitude of pressure oscillation was found to scale logarithmically the sensor $t_{90}$ response times.

In addition to sensor output corrections associated with the electronic interrogation of a sensor as described above, devices and systems hereof may also be operable to or adapted to apply one or more corrections to sensor output determined as a result of the flow path/blockage test. In that regard, sensors may, for example, be thought of as "molecule counters". Analytical sensors are thus calibrated in a manner that a certain amount of analyte molecules react at the analytical working or sensing electrode(s) as they diffuse through the instrument and measured values are converted to, for example, a part per million (ppm) or percentage based equivalent readings based upon previous calibration. When a porous member or barrier associated with a sensor inlet is open and unobstructed, rates of diffusion are very repeatable under the same conditions. As a porous member becomes blocked or flow paths are otherwise obstructed, the rate at which the molecules can diffuse from outside the instrument housing to the sensor can slow, thus lowering the rate at which molecules will encounter the active portion of the sensor, and thereby lowering the output. By measuring partial blockages as a result of one or more tests hereof, one can adjust the sensitivity of the sensor to maintain accurate readings regardless of such partial blockages.

Percent blockage may, for example, be readily experimentally correlated with a correction factor. An associated lookup table or an associated algorithm/formula may, for example, be stored in memory of the devise and systems hereof, and a correction factor for sensor sensitivity may be determined therefrom.

Figure 4A:
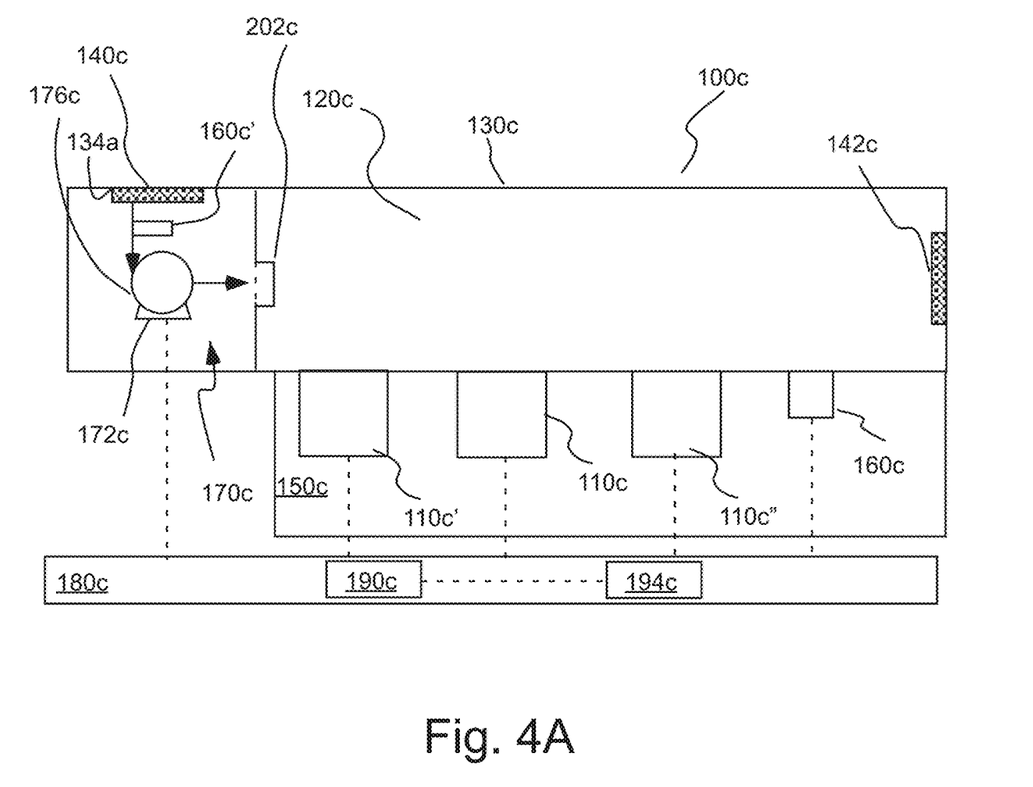
FIG. 4A illustrates another embodiment of a gas sensor device or instrument hereof similar in construction and operation to the device of FIG. 2B wherein pressure of ambient gas supplied by a sampling pump may be varied and a response of a pressure sensor within an inner chamber of the device is measured and the sampling pump in positioned within the inner chamber.

FIG. 4A illustrates another embodiment of a device or instrument 100c which, in a number of respects, is similar in operation and construction to device or instrument 100b. Elements of device 100c are numbered similarly to corresponding elements of device 100b, but the designation "b" is replaced with the designation "c". Like device 100b, device 100c is designed so that multiple sensors (three sensors 110c, 110c' and 110c" in the illustrated embodiment) are in fluid connection with inner chamber 120c, which allows gas to pass through and keeps water and other debris from the atmosphere out. The three sensors share a common inlet port (via porous member or membrane 140c). The three sensors also share the same internal or inner chamber 120c within the instrument, which is sealed everywhere such that the only path for air flow inflow is through porous member or membrane 140c. Gas exits inner chamber 120c via a second porous member 142c.

In device or instrument 100c, ambient environment is drawn through porous member 140c via sampling pump 176c including a pump motor 172c. Sampling pump 176c draws ambient gas through porous member 140c into a first section of inner chamber 120c which is connected to the remainder of inner chamber 120c via a port 202c. Three sensors 110c, 110c', and 110c", as well as pressure sensor 160c, are in fluid connection with chamber 120c, which allows gas to pass through and keeps water and other debris from the atmosphere out. As described above, the three sensors and pressure sensor 160c share a common outlet port (via porous member 142c), which is the only path for air flow out. In a sensing mode (in which device 100c is operated to sense analyte or target gas), sampling pump 176c is typically controlled to provide a constant or substantially constant pressure/flow rate. In an interrogation mode (in which device 100c is operated to detect blockage of porous member 140c), sampling pump 176c may be controlled via control circuitry, control system or controller 180c to create one or more pressure changes/pulses or to vary pressure in, for example, an oscillatory or sinusoidal fashion. Pressure data over time may be collected via pressure sensor 160c as described above. A pressure sensor analysis essentially identical to that described above may be used to determine if porous member or membrane 140c or porous member 142c is partially or completely blocked.

In another embodiment, a pressure sensor 160c' may be placed with inner chamber 120c to be in line with sampling pump flow from the ambient environment through porous member 140c. In an interrogation mode, sampling pump 176c may be controlled via control circuitry, control system or controller 180c to create one or more pressure changes/pulses or to vary pressure in, for example, an oscillatory or sinusoidal fashion. Pressure data over time may be collected via pressure sensor 160c' as described above. A pressure sensor analysis essentially identical to that described above may be used to determine if porous member or membrane 140c or 142c is partially or completely blocked. Pressure sensors 160c and 160c' may be used independently, or in combination.

Figure 4B:
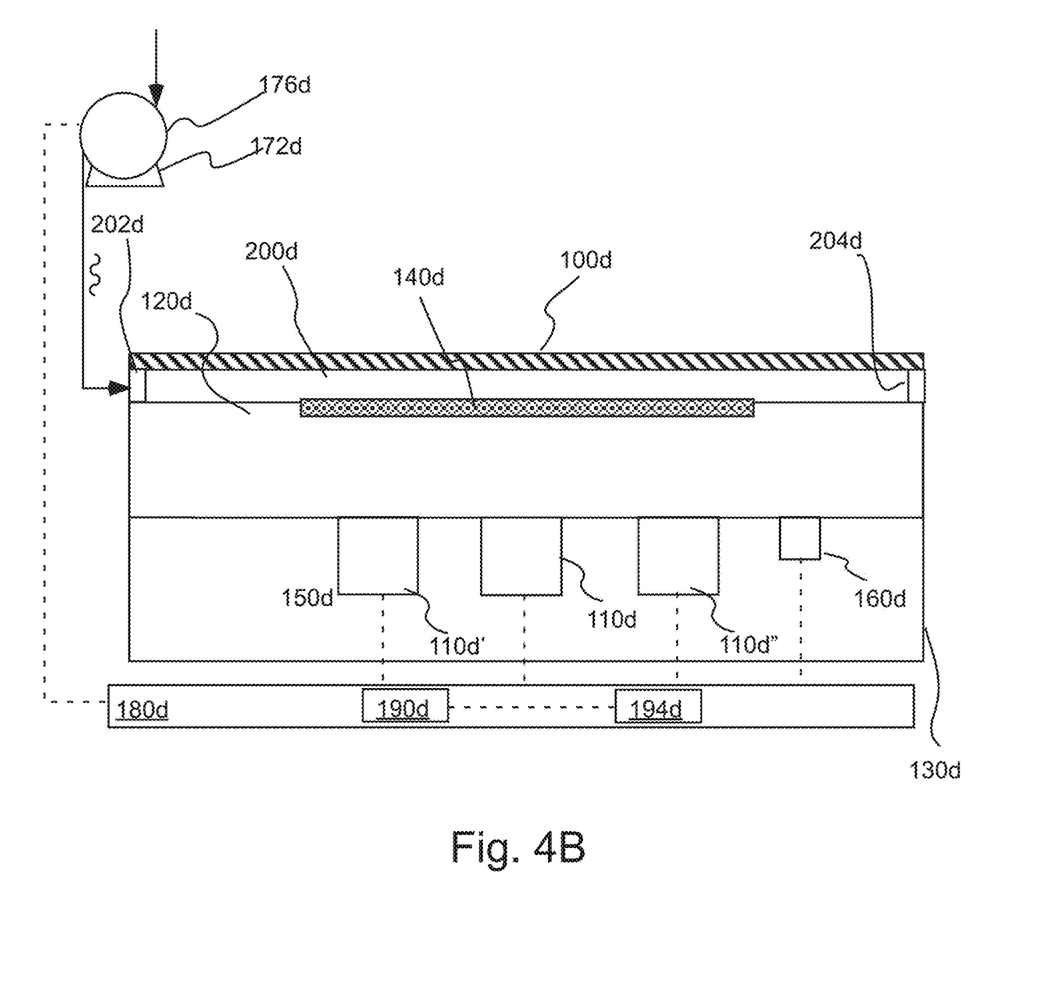
FIG. 4B illustrates another embodiment of a gas sensor device or instrument hereof similar in construction and operation to the device of FIG. 2B wherein pressure of ambient gas supplied by a sampling pump may be varied and a response of a pressure sensor within an inner chamber of the device is measured and the sampling pump in positioned outside of the inner chamber.

FIG. 4B illustrates another embodiment of a device or instrument 100d which, in a number of respects, is similar in operation and construction to device or instrument 100b. Elements of device 100d are numbered similarly to corresponding elements of device 100b, but the designation "b" is replaced with the designation "d". Like device 100b, device 100d is designed so that multiple sensors (three sensors 110d, 110d' and 110d" in the illustrated embodiment) are in fluid connection with chamber 120d, which allows gas to pass through and keeps water and other debris from the atmosphere out. The three sensors share a common inlet (via porous member or membrane 140d). The three sensors also share the same internal volume within the instrument, which is sealed everywhere such that the only path for air flow is through porous member or membrane 140d.

Device or instrument 100d further includes a plenum or manifold 200d which supplies a test gas (via pumping from sampling pump 176c) to sensors 110c, 110c' and 110c" in fluid connection with plenum 200d. Test gas from the ambient environment is forced through plenum 200d (entering plenum 200d via an inlet 202d and exiting plenum 200d via an outlet 204d) via sampling pump 176d including a pump motor 172d. Sampling pump 176d is in fluid connection with the ambient atmosphere and with plenum 200d.

In a sensing mode, sampling pump 176d is typically controlled to provide a constant or substantially constant pressure/flow rate. In an interrogation mode, sampling pump 176d may be controlled via control circuitry, control system or controller 180d to create one or more pressure changes/pulses or to vary pressure in, for example, an oscillatory or sinusoidal fashion. For example, sampling pump may be made "pulsatile", superimposing an oscillating pressure on the substantially constant pressure generation. Pressure data over time may be collected via pressure sensor 160d as described above. A pressure sensor analysis essentially identical to that described above may be used to determine if porous member or membrane 140d is partially or completely blocked.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of detecting at least a partial blockage in a porous member separating an inner chamber of a device, in which at least one gas sensor responsive to target gas is positioned, and an ambient environment, comprising:
emitting one or more pressure waves within the inner chamber by displacing a volume of the inner chamber via displacement of a moveable element in fluid connection with the inner chamber to create a predetermined volume displacement of the inner chamber to emit the one or more pressure waves, measuring a response via a pressure sensor responsive to the one or more pressure waves positioned within the inner chamber, and determining if at least a partial blockage is present in the porous member based upon the response of the pressure sensor.

2. The method of claim 1 wherein the moveable element comprises a piston.

3. The method of claim 1 wherein the moveable element comprises a diaphragm.

4. The method of claim 1 wherein the porous member is a porous frit or a porous polymeric membrane.

5. The method of claim 1 wherein the moveable element is moved to create a volume displacement of at least 1.5% of the volume of the inner chamber to emit the one or more pressure waves.

6. The method of claim 1 further comprising displacing the moveable element via a drive system in operative connection with the moveable element.

7. The method of claim 6 wherein the drive system comprises a motor in operative connection with the moveable element.

8. The method of claim 7 further comprising controlling the drive system to oscillate the motion of the moveable element.

9. The method of claim 8 wherein the drive system is controlled to oscillate the moveable element in a generally sinusoidal manner during an interrogation mode.

10. The method of claim 8 wherein the frequency of oscillation is less than 10 Hz.

11. The method of claim 8 wherein the frequency of oscillation is in the range of 1 Hz to 200 Hz.

12. The method of claim 11 wherein the moveable element comprises a diaphragm.

13. A gas sensor device to detect an analyte gas in an ambient environment, comprising:
   a housing comprising an inner chamber and a port;
   a porous member in operative connection with the port to separate the inner chamber from the ambient environment;
   at least one sensor responsive to a target gas positioned within the inner chamber;
   a source of pressure change in fluid connection with the inner chamber, the source of pressure change comprising a moveable element which is movable to displace a volume within the inner chamber;
   a drive system in operative connection with the moveable element and wherein the volume of the inner chamber is displaced by displacement of the moveable element via the drive system;
   a pressure sensor responsive to pressure change within the inner chamber; and
   circuitry in operative connection with the moveable element via the drive system to move the moveable element to create a predetermined volume displacement of the inner chamber to emit the one or more pressure waves, the circuitry further being in operative connection with the pressure sensor to determine if at least a partial blockage is present in the porous member based upon a response of the pressure sensor.

14. The gas sensor device of claim 13 wherein the drive system is operable to oscillate the motion of the moveable element.

15. The gas sensor device of claim 13 wherein the moveable element is moved to create a volume displacement of at least 1.5% of the volume of the inner chamber to emit the one or more pressure waves.

16. The gas sensor device of claim 13 wherein the volume of the inner chamber is displaced by displacement of the moveable element in fluid connection with the inner chamber.

17. The gas sensor device of claim 16 wherein the moveable element comprises a piston or a diaphragm.

* * * * *